United States Patent [19]

Maekawa et al.

[11] 4,060,685

[45] Nov. 29, 1977

[54] FURANACROYL ESTERS

[75] Inventors: Yukio Maekawa; Masato Satomura; Akira Umehara, all of Asaka, Japan

[73] Assignee: Fuji Photo Film Co., Ltd., Minami-ashigara, Japan

[21] Appl. No.: 680,994

[22] Filed: Apr. 28, 1976

Related U.S. Application Data

[62] Division of Ser. No. 414,609, Nov. 8, 1973, Pat. No. 3,993,624.

[30] Foreign Application Priority Data

Nov. 8, 1972 Japan .................................. 47-111804
Feb. 17, 1973 Japan .................................. 48-19544

[51] Int. Cl.$^2$ .................. C07D 407/06; C07D 407/10; C07D 407/12
[52] U.S. Cl. .............................. 542/413; 260/346.11; 260/347.5; 260/248.59
[58] Field of Search ............ 260/240 R, 347.4, 348 A, 260/240 R, 347.5

[56] References Cited

U.S. PATENT DOCUMENTS

| | | | |
|---|---|---|---|
| 2,196,746 | 4/1940 | Dickey et al. | 260/347.5 X |
| 2,436,532 | 2/1948 | Singleton | 260/347.5 X |
| 2,889,338 | 6/1959 | Dazzi | 260/348 A |
| 3,471,386 | 10/1969 | D'Alelio | 260/348 A X |
| 3,649,676 | 3/1972 | Galfre et al. | 260/348 A X |

OTHER PUBLICATIONS

Chem. Abstracts 77831d, vol. 69, 1968, "Synthesis . . . . of . . . allyl esters of some acids of furan series".
Chem. Abs. 86,054t, pp. 8073–8074, "Polymerization of Glycidyl Esters of the Furan Series", Krylova et al., vol. 66, 1967.

*Primary Examiner*—Allen B. Curtis
*Attorney, Agent, or Firm*—Sughrue, Rothwell, Mion, Zinn and Macpeak

[57] ABSTRACT

Light sensitive high molecular weight compounds containing furanacrylate groups in the molecule, which can be suitably used for the preparation of photopolymerizable compositions used in light sensitive materials such as, e.g., a photoresist, a method for forming images using the high molecular weight compounds which undergo a change in solubility or are rendered in soluble upon irradiation and a method for preparing the high molecular weight compounds containing the novel structure by homo- or copolymerization of a monomeric vinyl ether or epoxy compound containing a furanacrylate group in the molecule.

5 Claims, No Drawings

FURANACROYL ESTERS

This is a Division of application Ser. No. 414,609, filed Nov. 8, 1973, now U.S. Pat. No. 3,993,624.

BACKGROUND OF THE INVENTION

1. Field of the Invention

The present invention relates to a light-sensitive material containing a light-sensitive high molecular weight compound having a novel structure which undergoes a reduction in solubility or is rendered insoluble upon irradiation with light or an electron beam, to a method for forming images using this light-sensitive material, and to a process for the synthesis of the reactive high molecular weight compounds. More particularly, the present invention relates to photosensitive high molecular weight compounds containing furanacryloxy groups in the molecule.

2. Description of the Prior Art

Heretofore, high molecular weight compounds which undergo a reduction in solubility or which are rendered insoluble by the action of light or an electron beam have been studied. Detailed descriptions of such are given in the literature (e.g., see Kosar; *Light-Sensitive Systems*, John Wiley & Sons, New York (1965), and Schönbergs; *Photochemistry of Organic Synthesis*, Kodansha, Tokyo (1971) ). Among these studies, photo-dimerization-type high molecular weight compounds having a cinnamic ester structure $$(-O-\underset{\underset{O}{\|}}{C}-CH=CH-\bigcirc)$$

as the light-sensitive group have been well studied and are partly put into practice.

A light-sensitive group which is known to have a far higher sensitivity than the cinnamic ester group is a furanacrylic ester group $$(-O-\underset{\underset{O}{\|}}{C}-CH=CH-\underset{O}{\bigcirc}).$$

High molecular weight compounds having this structure have been synthesized using a high polymer reaction and have been actually confirmed to possess high sensitivity. (For example, see M. Tsuda; *J. Polymer Sci*, A - 1, 7, 259 (1969), and Nishikubo, Tomiyama, Maki, and Takaoka; *High Polymer Chemistry*, 29, No. 305, 295 (1972) )

On the other hand, as a result of various investigations to obtain a highly sensitive compound which undergoes a reduction in solubility or is rendered insoluble by the action of light or an electron beam and which is suitable for use as a light-sensitive element of light-sensitive materials, i.e., a compound which contains therein light-sensitive groups in an extremely high proportion, a compound in which the proportion of the light sensitive groups can be freely controlled and a compound to which various properties can easily be imparted, the inventors have discovered the fact that a high molecular weight compound having at least 3 mol % of the repeating structural unit which contains the furanacrylic ester structure and which is represented by the following general formula (I) or (II) has the above-described properties.

SUMMARY OF THE INVENTION

That is, the present invention comprises a light-sensitive high molecular weight compound capable of being cross-linked by the action of light or an electron beam with the high molecular weight compound containing at least 3 mol% of structural units represented by the following general formula (I) or (II);

$$\begin{array}{c} -(CH_2-CH)- \\ | \\ O-R_1-O-\underset{\underset{O}{\|}}{C}-CH=CH-\underset{O}{\bigcirc}-R_3 \end{array} \quad (I)$$

$$\begin{array}{c} -(CH_2-CH-O)- \\ | \\ CH_2-R_2-O-\underset{\underset{O}{\|}}{C}-CH=CH-\underset{O}{\bigcirc}-R_3 \end{array} \quad (II)$$

wherein $R_1$ represents $$-(CH)_{\overline{m}}(CH_2)_{\overline{n}},\ -CH_2CH_2-(OCH_2CH_2)_{\overline{n}},$$
$$\overset{|}{CH_3}$$

$$-(CH)_{\overline{m}}(CH_2)_{\overline{n}}-O-\bigcirc-(CH_2)_{\overline{n}},\ \text{or}$$
$$\overset{|}{CH_3}$$

$$-(CH_2)_{\overline{n}}-\bigcirc-(CH_2)_{\overline{n}};$$

$R_2$ represents $$-(CH_2)_{\overline{m}}-,\ -(CH)_{\overline{m}}-(CH_2)_{\overline{n}}-,$$
$$\overset{|}{CH_3}$$

$$-O-(CH_2)_{\overline{n}}-(CH)_{\overline{m}}-,\ -(OCH_2CH_2)_{\overline{n}}-,$$
$$\overset{|}{CH_3}$$

$$-O-(CH)_{\overline{m}}-(CH_2)_{\overline{n}}-O-\bigcirc-(CH_2)_{\overline{n}}-,$$
$$\overset{|}{CH_3}$$

$$-O-\bigcirc-(CH_2)_{\overline{n}}-,$$

$$-O-CH_2CH_2-O-\bigcirc-CH_2-;$$

$R_3$ represents —H, —$CH_3$, —$C_2H_5$, —Cl, or —Br, $m$ represents 0 or 1, and $n$ represents an integer of 1 to 4.

DETAILED DESCRIPTION OF THE INVENTION

As the high molecular weight compounds having the structural unit represented by the general formula (I), there are those obtained by homopolymerizing a vinyl monomer represented by the following general formula (I');

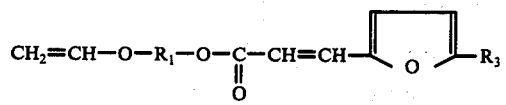 (I')

wherein $R_1$ and $R_3$ are the same as defined before, or by copolymerizing the above-described monomer with one or more additional vinyl monomers.

As the high molecular weight compounds having the structural unit represented by the general formula (II), there are those obtained by the ring-opening homopolymerization of an epoxy compound represented by the following general formula (II');

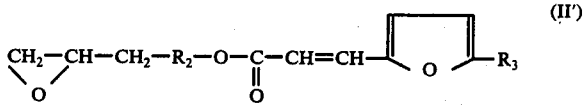 (II')

wherein $R_2$ and $R_3$ are the same as defined before, or by the ring-opening copolymerization of the above-described epoxy compound and one or more additional monomers which have the property of ring-opening polymerization.

The vinyl monomer of the general formula (I') and the general formula (II') can be synthesized by, e.g., (1) reacting a halogen-containing (e.g., chlorine, bromine or iodine containing, with chlorine and bromine being preferred) vinyl ether or epoxy compound with an alkali metal salt (e.g., the sodium, potassium or lithium salt with the sodium or potassium salt being preferred) of a substituted or unsubstituted furanacrylic acid having the general formula

where $R_3$ is a hydrogen atom, a lower alkyl group such as a methyl group, an ethyl group, or a halogen atom such as a chlorine atom or a bromine atom with a hydrogen atom being preferred, in the presence of a quaternary ammonium salt, or (2) reacting a hydroxyl group-containing vinyl ether or epoxy compound with a substituted or unsubstituted furanacryl halide having the general formula

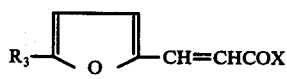

where $R_3$ is as above defined and X is a halogen atom, e.g., a chlorine atom or a bromine atom with chlorine being the most preferred in the presence of an organic or inorganic base.

Specific examples of suitable furanacrylic acids which can be employed are

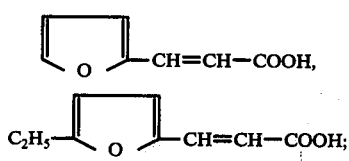

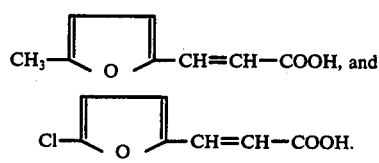

Appropriate quaternary ammonium salts for process (1) are

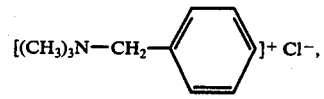

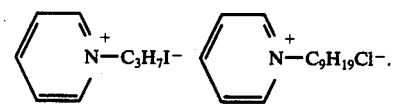

The acid halides and particularly the acid chlorides of the above described specific examples of furanacylic acids are suitable examples of the furanacryl halides for process (2).

Suitable examples of organic and inorganic bases which can be used in process (2) are pyridine, triethyl amine, sodium hydroxide, potassium hydroxide, dimethylamiline, diethylaniline, triethylene diamine, picoline, quinoline, isoquinoline, etc.

The aforesaid halogen-containing vinyl ether and epoxy compounds can be exemplified by the following compounds:

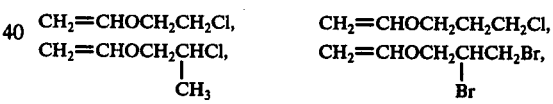

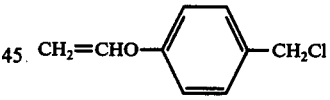

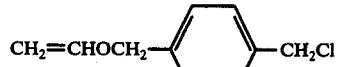

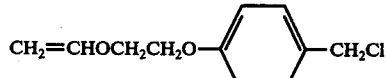

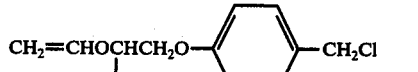

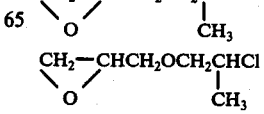

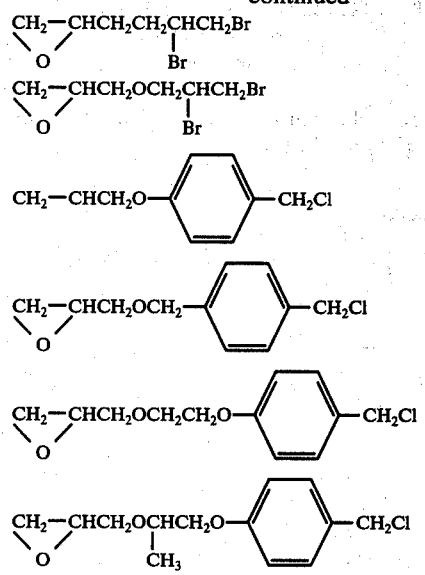

The hydroxy group-containing vinyl ether and epoxy compounds can be exemplified by the following compounds:

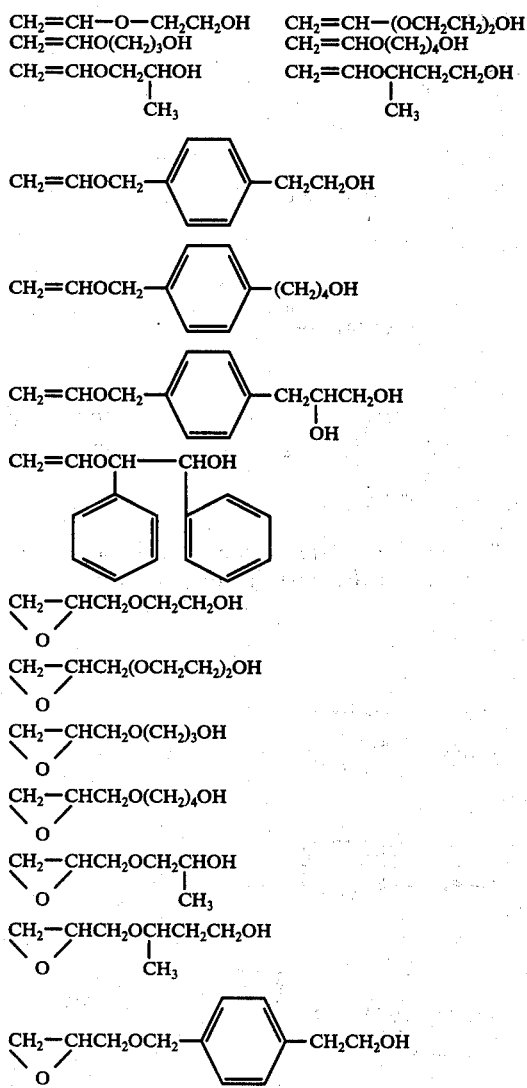

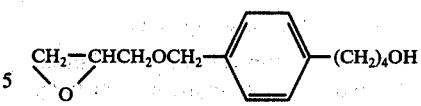

Some of the aforesaid compounds are described by Murahashi et al. in *Gosei Kobunshi (Synthetic High Molecules)*, published by Asakura Shoten (1971).

The substituent on the aforesaid substituted furanacrylic acid derivatives can be, e.g., methyl and ethyl group and chlorine and like halogen atoms.

In process (1) above the molar ratio of the halogen-containing vinyl ether or epoxy compound to the alkali metal salt of the substituted or unsubstituted furanacrylic acid generally employed ranges from about 0.1:1 to 30:1 preferably 1:1 to 1:15 and the temperatures of reaction usually employed are from about 50° to 180° C, preferably 100° to 150° C. The process is conducted preferably in a solvent such as benzene, toluene, pyridine, dioxane, xylene, ethylbenzene, durene, diphenylether, anisole, etc. boiling above 80° C, preferably above 100° C, with a quaternary ammonium salt concentration of generally about 2 to 20 mole %, preferably 3 to 10 mole %, to the alkali metal salt of the furanacrylic acid.

In process (2) above the molar ratio of the hydroxyl group containing vinyl ether or epoxy compound to the substituted or unsubstituted furanacryl halide generally employed ranges from about 0.1:1 to 20:1, preferably 0.5:1 to 2:1 and the temperatures of reaction generally employed range from about 0° to 150° C, preferably 20° to 100° C. The process is usually conducted in chlorinated hydrocarbons, hydrocarbons or ketones such a chloroform, carbon tetrachloride, hexane, cyclohexane, methyl ethyl ketone, etc. with an inorganic or organic base concentration ranging from 0.5 to 30 mole %, preferably 2 to 10 mole %, to the hydroxyl group containing vinyl ether or expoxy compound.

The following examples are illustrative of the synthesis of monomers of the general formula (I') or (II') in the processes as described above. Unless otherwise indicated all parts and percents hereinafter are by weight.

MONOMER SYNTHESIS EXAMPLE A

Synthesis of Beta-vinyloxyethyl Furanacrylate

In a three-necked flask equipped with a Simroe cooler there were charged 32 g of sodium furanacrylate, 180 ml of chloroethyl vinyl ether, 1.0 g of trimethylbenzylammonium chloride and 0.5 g of phenylnaphthylamine as a polymerization inhibitor, and the mixture was vigorously stirred at 110° to 120° C for 5 hours. The sodium chloride formed during the reaction was separated by filtration and washed with 20 ml of chloroethyl vinyl ether. The washing was combined with the filtrate and distilled under reduced pressure (e.g. 1–50 mm Hg, preferably 10–20 mm Hg) to recover the excess chloroethyl vinyl ether. The residue was then rectified under reduced pressure to obtain 21 g of a colorless oil. The oil was allowed to stand to effect crystallization. The crystals were recrystallized from n-hexane to obtain the end product having a melting point of 39°–40° C in a yield of 50%.

MONOMER SYNTHESIS EXAMPLE B

Synthesis of Glycidyl Furanacrylate

In a three-necked flask equipped with a Simroe cooler there were charged 32 g of sodium furanacrylate, 180 g of epichlorohydrine, 0.2 g of trimethyl benzylammonium chloride and 0.2 g of phenyl naphthylamine and the mixture was vigorously stirred at 110° to 120° C for 5 hours. The sodium chloride formed was separated by filtration and washed with 20 g of epichlorohydrin. The washing was combined with the filtrate and distilled under reduced pressure to recover the excess epichlorohydrin. The residue was rectified twice to obtain 36 g of a colorless viscous liquid having a boiling point of 110° to 111° C/1 mm Hg as the end product in a yield of 83%.

Specific examples of the monomer represented by the general formula (I') are illustrated below.

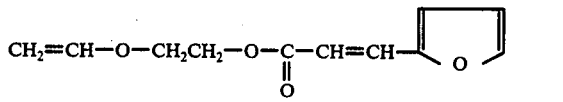

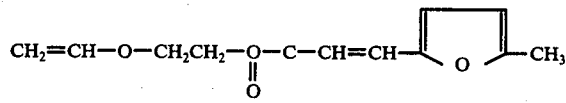

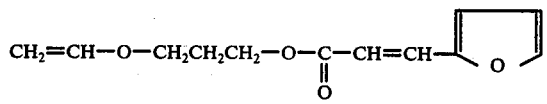

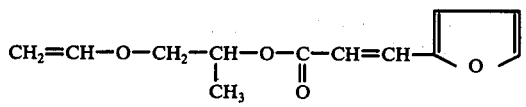

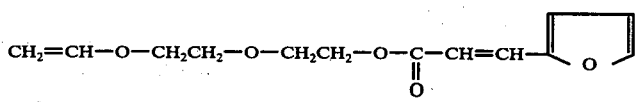

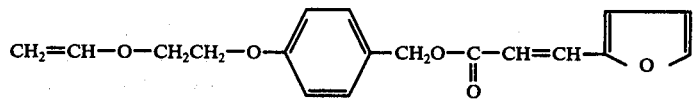

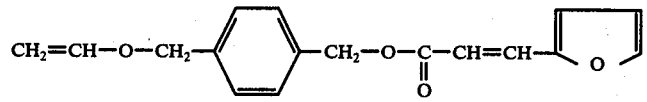

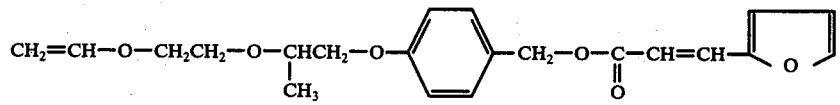

Specific examples of the epoxy compound represented by the general formula (II') are illustrated below.

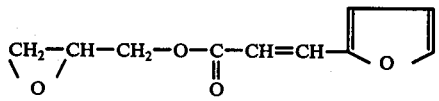

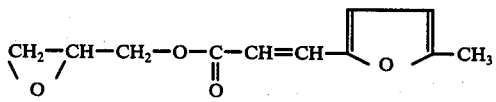

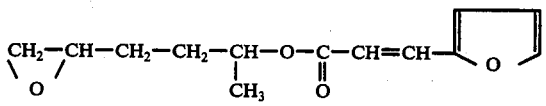

-continued

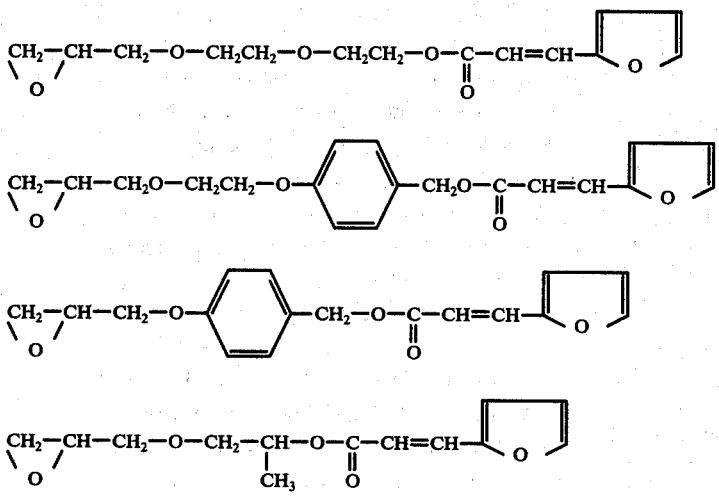

The reactive high molecular weight compounds containing therein structured units of the general formula (I) or (II) are synthesized by polymerizing the vinyl ether or epoxy compound containing a furanacrylate group of the general formula (I') or (II'), either alone or in combination with other monomers copolymerizable therewith.

The copolymerizable monomer which can be suitably used is any of the polymerizable monomers capable of copolymerizing with the vinyl ether or epoxy monomer compound, such as, e.g., in case of vinyl ethers containing a furanacrylic ester group of the general formula (I'), n-propyl vinyl ether, isobutyl vinyl ether, chloroethyl vinyl ether, phenyl vinyl ether, 2-naphthyl vinyl ether, styrene, α-methylstyrene, methyl acrylate, methyl methacrylate, vinyl chloride, vinylidene chloride, acrylonitrile, acrylamide, butadiene, isoprene and the like; and, in case of the epoxy compounds containing a furanacrylic ester group of the general formula (II'), ethylene oxide, propylene oxide, butylene oxide, phenyl glycidyl ether, 3,3-bis-chlorooxetane, tetrahydrofuran, 1,3-dioxolan, trioxane, maleic anhydride, succinic anhydride and the like. Mixtures of such monomers within the above described groups can also be used.

The copolymerizable monomer can be used in widely varying proportions amounting to up to 95%, preferably up to 90%, by weight of the light sensitive high molecular weight compound obtained. Where the high molecular weight compound is a copolymer, however, it is necessary that the copolymer contain at least 3 mol% of furanacrylic ester structure represented by the general formula (I) or (II). If the content of the furanacrylic ester structure is less than that, it is difficult for the copolymer to show necessary photocross-linking reactivity for light-sensitive material. Therefore, the charging ratio of monomers must be decided with this point in mind.

The polymerization catalyst suitably used in the polymerization, e.g., the homo- or copolymerization, of the monomers represented by the general formula (I') or (II') includes, e.g., Lewis acids or proton acids such as boron trifluoride and its etherates, zinc chloride, diethylzinc, aluminum chloride, triethylaluminum, ethylaluminum dichloride, aluminum isopropoxide, ferric chloride, stannic chloride, anhydrous hydrogen chloride, sulfuric acid, trifluoroacetic acid and metallic sulfates such as aluminum sulfate. These may be used alone or in combination.

For the monomers represented by the general formula (I'), radical polymerization catalysts such as benzoyl peroxide, azobisisobutyronitrile or the like can be used.

In addition, for the epoxy compounds represented by the general formula (II'), well known promoters such as ethylene oxide and propylene oxide may also be used.

These polymerization catalysts are preferably used in an amount of from about 0.1 to about 10 mol% based on the monomer or monomers of the general formula (I') or (II').

The polymerization can be carried out in either bulk or solution polymerization. In the solution polymerization process, aromatic hydrocarbons and chlorinated hydrocarbons having boiling points of 50° to 150° C, such as, e.g., methylene chloride, carbon tetrachloride, toluene, benzene or nitrobenzene can suitably be used. The solvent can be used in an amount of 0.1 to 90, preferably 1 to 50% by weight of the vinyl ether or epoxy compound containing the furanacrylate group.

Where the polymerization is effected in solution, the concentration of the monomer or monomers is suitably from about 1 to 80% (by weight). The polymerization temperature is generally within the range of from about −100° to +150° C. Where monomer represented by the general formula (I') is used, it is particularly preferable to conduct the polymerization at −78° to 0° C, while where monomer represented by the general formula (II') is used, it is particularly preferable to effect the polymerization at −78° to +80° C.

Details of the polymerization procedure are described by Higashimura et al. in *Kobunshi Kaguku* (*High Molecular Chemistry*) I, vol. 16 of *Kindai Kogyo Kaku* (*Recent Industrial Chemistry*) Series, published by Asakura Shoten in 1967, and using a vinyl ether compound in U.S. Pat. Nos. 2,825,719; 2,830,032; 2,967,166; 3,088,079; 2,616,879; 3,159,613; 3,062,789; 3,156,680; and 3,098,061; and using an epoxy compound in U.S. Pat. Nos. 2,706,181; 2,934,505; 2,917,470; 2,844,545; 2,861,962; 3,135,705; 2,870,100; 2,722,520; 2,909,492; 2,895,924 and 3,409,593.

In the monomer of the general formula (I') or (II') containing the furanacrylic ester group as used in the present invention, e.g., in a vinyl ether compound of the general formula (I'), the vinyl group in the vinyl ether moiety, the carbon-to-carbon double bond in the furanacrylic ester moiety and the furan ring may be regarded as active sites, and, in particular, the furan ring is known to be cation polymerizable since it is an intracyclic vinyl ether, though, even if the compound is polymerized by the aid of a cationic polymerization catalyst, the polymerization proceeds without gelation to completion to yield a polymerizate soluble in benzene, tetrahydrofuran or a like organic solvent. In addition, the high molecular weight compound synthesized in accordance with the process described above exhibits infrared absorption bands characteristic of the furan ring, e.g., at 3,130 cm$^{-1}$, 1,560 cm$^{-1}$, 1,030 cm$^{-1}$ and 880 cm$^{-1}$, indicating that in the polymerization takes place selectively at the vinyl ether or epoxy groups.

In the present invention the concentration of the photosensitive groups in the end product can easily be controlled freely by appropriately changing the ratio of the furanacrylic ester group-containing monomer of the general formula (I') or (II') to the comonomer, since the synthesis process used is a polymerization technique. In addition, it is possible to synthesize high molecular weight compound containing units of the general formula (I) or (II) having various characteristics and properties, i.e. different in solubility, adhesiveness or other properties, by an appropriate choice of comonomer.

The thus synthesized light-sensitive high molecular weight compound undergoes a reduction in solubility or is rendered insoluble by the action of light or an electron beam. A suitable wave length which can be employed is a wave length of about 50 to 800 mμ, preferably 100 to 500 mμ.

As to the reaction mechanism upon irradiation, a four-membered ring-forming reaction is believed to occur as in the case of high molecular weight compounds containing the conventional cinnamic ester structure group.

While the high molecular weight compound used in the present invention is particularly useful as a light sensitive composition, it is possible to shorten the irradiation time and to produce the desired difference in physical property by adding, as a sensitizing agent, an aromatic carbon compound, an aromatic nitro compound, an aromatic quinone, a triphenyl methane, an anthrone, a nitroaniline, an acylated nitroaniline, a thiazole, a benzoylmethylene, β-naphthothiazoline, a ketone or various photographic sensitizing dyes.

Specific examples of such useful sensitizing compounds are nitro compounds such as p-nitrodiphenyl, 5-nitro-2-aminotoluene-4-nitro-1-aminoathalene, 4-nitro-1-acetylaminonaphthalene, picric acid, picramide, dichloronitroanilene, nitroacenaphthene, dinitronaphthalene, trinitrofluorenone, tetranitrocarbazole, dinitrobenzoanthrazenedione, dinitrodimethylacetyl-tert-butylbenzene, dinitrostilbene disulfonic acid, trinitronaphthalene, and dinitrochalcone, carbonyl compounds such as benzanthrone, 9-anthraldehyde, acetonaphthone, xanthone, benzophenone, tetramethylaminobenzophenone, tetraethylaminobenzophenone, dimethoxybenzophenone, dimethoxythiobenzophenone, 1-cyano-2-keto-3-methyl-6-bromo-3-azabenzathrone, 1-carboethoxy-2-keto-3,4-diazabenzanthrone, 2-keto-3-methyl-1,3-diazabenzanthrone, diphthaloylnaphthalene, 2-benzoylmethylene-1-β-naphthothiazoline, 4-H-quinolizine-4-thione, phenanthrenquinone, benzanthraquinone, t-butylanthraquinone, chloroanthraquinone, 2-benzoylmethylene-1-methyl-benzothiazoline, 2-nitrophthaloylmethylene-1-ethylbenzothiazoline, dimethylcarbamoylmethyleneethylbenzothiazoline, diethylcarbamoylmethyleneethylbenzothiazoline, and dyes such as methyl violet, victoria blue, malachite green, (triphenylmethane dyes) diethyldibenzothiacyanine iodide, diethyldibenzothiacarbocyanine bromide, dimethyldibenzothiacyanine iodide (cyanine, thiocyanine dyes). Other compounds such as methyl-3-ethyl-2-benzothiazolinylidene dithioacetate,2,6-di(p-ethoxyphenyl)-4-(p-n-amyloxyphenyl)-thiapyryliumperchorate (pyrylium salts) are also suitable. Some of these compounds are described in U.S. Pat. Nos. 3,475,617; 3,737,319; 3,453,110; 3,409,593; 3,575,929; 2,835,656; 3,357,831; 3,418,295; 3,647,470; 2,956,878; 3,173,787; 3,023,100; and 3,066,117, and British Pat. No. 659,197. These sensitizers can be used in a proportion of about 1 to 20% (by weight) based on the weight of the high molecular weight compound. Preferred examples of such sensitizers are N,N-diethylamino-p-benzophenone, N,N'-dimethylamino-p-benzophenone, 5-nitroacenaphthene, 2-nitrofluorene, N-acetyl-4-nitro-1-naphthylamine, etc.

In order to form images using the above-described high molecular weight compound of the present invention, the high molecular weight compound is dissolved, together with the above-described sensitizer, in a solvent therefor such as a ketone solvent, an amide solvent, a halogenated aliphatic or aromatic solvent such as chlorobenzene, dichlorobenzene, trichlene, an ether solvent such as anisole, a cellosolve solvent, or a mixture thereof, preferably in a proportion of about 1 to 15% (by weight), and the resulting solution is applied in an amount of about 0.1 to 5 g of the high molecular weight compound/m², preferably 0.2 to 1 g/m², to a support such as high molecular weight films or metal substrates (e.g., a polyethylene terephthalate film, a zinc plate or a aluminum plate for use in printing, a silicon wafer, etc.) using dip-coating, rod coating, spinner coating, spray coating or a like coating method to thereby prepare a light-sensitive plate.

The thus obtained light-sensitive plate is then imagewise exposed through an original which is superposed thereon, and is processed with a solvent or a solvent containing a dye such as

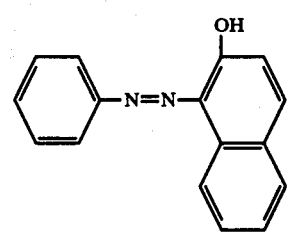

Sudan Orange R(1-phenylazo-2-naphthtol) produced by Badische Anilin Soda-Fabrik, Germany Color Index. Solvent Yellow 14. 12055 or a pigment

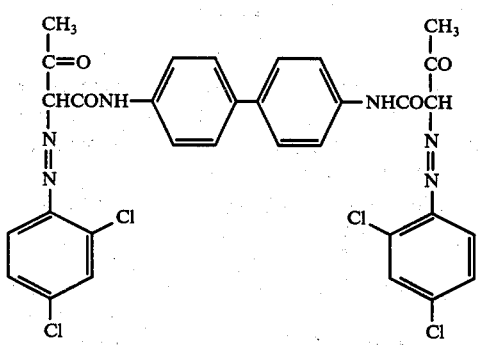

Permanent Yellow NCG color Index Pigment Yellow 16, 20040 Gabwerke Hoechst A.G. Germany. The high molecular weight compound at the unexposed areas does not undergo a photohardening reaction and is dissolved away into the solvent. When a dye or pigment is used, it adheres to the dissolved areas to form an image. Suitable dyes or pigments are oil-soluble dyes or pigments.

Since the light-sensitive high molecular weight compound used in the present invention is synthesized by the polymerization of monomer or monomers represented by the general formula (I') or (II'), the light-sensitive group can be introduced into the high molecular weight compound with ease in various proportions, and hence the light sensitivity of the high molecular compound can be adjusted as desired. For example, an extremely highly sensitive high molecular compound wherein all the repeating units have the light-sensitive group can be prepared by homopolymerizing the monomer (I') or (II'). In addition, various physical properties can be imparted to said high molecular compound by changing the kind and the proportion of the comonomer or comonomers to be used.

The present invention will now be described in more detail by reference the following polymer synthesis examples of the light-sensitive high molecular compound of the present invention and the examples of image formation using the light-sensitive high molecular weight compounds of the present invention.

POLYMER SYNTHESIS EXAMPLE 1

A glass polymerization vessel purged of air with a dry inert gas (such as nitrogen, argon, neon, ethane, propane, methane, etc.) was charged with 1.0 g of beta-vinyloxyethyl furanacrylate and 4.0 ml of methylene chloride and, at a temperature of $-78°$ C, an amount, corresponding to 4 mol % of the beta-vinyloxyethyl furanacrylate charged, of boron trifluoride-ether complex as a solution in methylene chloride of a concentration of $4.3 \times 10^{-4}$ mol/ml. The mixture was maintained at $-78°$ C for 1 hour and then stirred into an excess of an ammonical methanol to precipitate a high molecular weight compound white in color. The high molecular weight compound was soluble in benzene, tetrahydrofuran and methyl ethyl ketone. The precipitate was recovered by filtration and dried at room temperature in vacuo to obtain 0.85 g of a high molecular weight compound having an intrinsic viscosity, determined in tetrahydrofuran solution at 30° C, of 0.15 dl/g.

POLYMER SYNTHESIS EXAMPLE 2

The same procedure as described in Polymer Synthesis Example 1 was repeated except that there were used 1.0 g of beta-vinyloxyethyl furanacrylate, 0.5 g of isobutyl vinyl ether, 4.0 ml of methylene chloride and an amount, corresponding to 4 mol % of beta-vinyloxyethyl furanacrylate, of boron trifluoride-ether complex as a solution in methylene chloride in a concentration of $4.3 \times 10^{-4}$ mol/ml and the polymerization time was 2 hours.

Thus, there was obtained 0.90 g of a high molecular weight compound (90% yield) having an intrinsic viscosity (in tetrahydrofuran at 30° C) of 0.22 dl/g and soluble in benzene, tetrahydrofuran and methyl ethyl ketone.

POLYMER SYNTHESIS EXAMPLE 3

A glass polymerization vessel purged with a dry inert gas was charged with 1.0 g of glycidyl furanacrylate and 4 ml of n-hexane and then, at room temperature, an amount, corresponding to 5 mol% of glycidyl furanacrylate, of diethylzinc-water complex as a solution in n-hexane in a concentration of $2.7 \times 10^{-4}$ mol/ml. The mixture was allowed to stand at room temperature for 38 hours.

The mixture was then poured into an excess of petroleum ether and the precipitate formed was filtered, washed with petroleum ether, dried, washed with dilute aqueous ammonia (aqueous ammonia: water = 1:1) and, thereafter, with water repeatedly. The precipitate was then dried at room temperature in vacuo to recover 1.0 g (about 100% theoretical yield) of a high molecular weight compound having an intrinsic viscosity (in tetrahydrofuran at 30° C) of 0.08 dl/g and soluble in benzene, tetrahydrofuran and methyl ethyl ketone.

POLYMER SYNTHESIS EXAMPLE 4

In a similar manner as described in Polymer Synthesis Example 3 a copolymerization was carried out at room temperature for 142 hours using 0.2 g of glycidyl furanacrylate, 1.8 g of propylene oxide, 6.0 ml of n-hexane and an amount, corresponding to 5 mol %, of diethylzinc-water complex, as a solution in n-hexane in a concentration of $2.7 \times 10^{-4}$ mol/ml.

Thus, there was obtained 2.0 g of a high molecular weight compound having an intrinsic viscosity (in tetrahydrofuran at 30° C) of 0.53 dl/g and soluble in benzene, tetrahydrofuran and methyl ethyl ketone.

POLYMER SYNTHESIS EXAMPLE 5

In a glass vessel purged of air with a dry inert gas there were charged 20 ml of a ferric chloride-propylene oxide complex and 1.0 g of glycidyl furanacrylate and the charge was allowed to stand at 80° C for 165 hours. The charge was then poured into a large amount of petroleum ether and the precipitate recovered was washed with petroleum ether, dried, washed with dilute hydrochloric acid (1:1 mixture of a conc.hydrochloric acid and water) and washed repeatedly with water.

Thus, there was obtained 1.0 g (theoretical yield) of a high molecular weight polymer which also was soluble in benzene, tetrahydrofuran and methyl ethyl ketone and had an intrinsic viscosity as measured in solution in tetrahydrofuran at 30° C of 0.12 dl/g.

EXAMPLE 1

A 5% (by weight) methyl ethyl ketone solution was prepared using the high molecular weight compound obtained in Polymer Synthesis Example 1. To this was added N,N'-diethylamino-p-benzophenone as a sensitizer in a proportion of 5% (by weight) based on the weight of the high molecular weight compound and stirred to dissolve the compound completely.

The resulting solution was applied under a safe light to a surface-processed aluminum plate using a No. 26 coating road and allowed to dry at room temperature (about 20°–30° C). Then, the plate was maintained at 70° C for 5 minutes so that it could dry completely. The thus obtained light-sensitive plate was irradiated through a line original superposed thereon for 5 seconds using a 450 W high pressure mercury lamp spaced at a distance of 28 cm. When the plate was processed with methyl ethyl ketone solution, the light-struck area was found to be cross-linked and rendered insoluble in the methyl ethyl ketone solution. This was confirmed by further processing the plate with an oil-soluble dye whereby only the exposed area was colored.

EXAMPLE 2

This Example describes the use of the high molecular weight compound obtained in Polymer Synthesis Example 1 without a sensitizing dye.

A 5% (by weight) methyl ethyl ketone solution of the high molecular weight compound obtained in Polymer Synthesis Example 1 was prepared as described in Example 1, without adding the sensitizer.

The resulting solution was applied under a safe light to a surface-processed aluminum plate using a No. 26 coating rod and dried. When the resulting light-sensitive plate was irradiated for 5 minutes through a line original superposed thereon using a 450 W high pressure mercury lamp spaced at a distance of 28 cm and processed with methyl ethyl ketone, a distinct image also was obtained.

Additionally, when irradiation was effected for 5 seconds as described in Example 1, no insolubilization occurred and no image was obtained. From this, it can be seen that the N,N'-diethylamino-p-benzophenone used in Example 1 clearly served to markedly shorten the irradiation time.

EXAMPLE 3

A 6% (by weight) chlorobenzene solution was prepared using the high molecular weight compound obtained in Polymer Synthesis Example 2.

To this was added 2-nitrofluorene, as a sensitizer, in a proportion of 8% (by weight) based on the weight of the high molecular weight compound and dissolved therein.

The resulting solution was applied under a safe light to a surface-processed aluminum plate using dip-coating and the plate was allowed to dry at a room temperature. Then, the plate was maintained at 70° C for 5 minutes for complete drying. The thus obtained light-sensitive plate was irradiated for 5 seconds through a line original superposed thereon using a 450 W high pressure mercury lamp spaced at a distance of 28 cm. When this plate was processed with methyl ethyl ketone, the exposed area was found to be rendered insoluble. Upon drying, a distinct image was found to be formed.

Additionally, when a light-sensitive plate prepare as described above but without the 2-nitrofluorene was exposed as described in Example 2, the light-sensitive layer was not rendered insoluble by the exposure for 10 seconds, but was rendered insoluble by exposure for 5 minutes to form an image. Thus, it is clear that the sensitizer markedly shortens the exposure time.

EXAMPLE 4

A 10% (by weight) methyl cellosolve solution was prepared using the high molecular weight compound obtained in Polymer Synthesis Example 3. To this was added as a sensitizer 7% (by weight) of Michler's ketone and the materials dissolved completely.

When the resulting solution was applied to a polyethylene terephthalate sheet in the laboratory in day light and was left for 2 hours while superposing thereon a step wedge having a step difference of 0.11 to 0.16, the light-sensitive layer became insoluble up to the second step and was not dissolved in methyl ethyl ketone, benzene, chlorobenzene or a like solvent.

EXAMPLE 5

A 10% (by weight) trichlene solution was prepared using the high molecular weight compound obtained in Polymer Synthesis Example 4. To this was added 5-nitroacenaphthene, as a sensitizer, in a proportion of 5% (by weight) based on the weight of the high molecular weight compound and stirred to dissolve the materials completely.

The resulting solution was applied under a safe light to a surface-processed aluminum plate using a No. 26 coating rod and the plate was allowed to dry at a room temperature. Then, the plate was maintained at 70° C for 5 minutes for complete drying. The thus obtained light-sensitive plate was irradiated for 1 minute through a step wedge having a step difference of 0.11–0.16 superposed thereon, using a 450 W high pressure mercury lamp spaced at a distance of 28 cm. When the plate was processed with methyl ethyl ketone, the light-sensitive layer was rendered insoluble up to fifth step.

While the invention has been described in detail and with reference to specific embodiments thereof, it will be apparent to one skilled in the art that various changes and modifications can be made therein without departing from the spirit and scope thereof.

What is claimed is:

1. A furanacroyl ester having the general formula

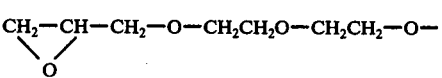

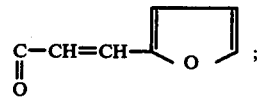

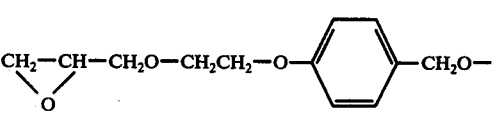

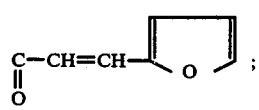

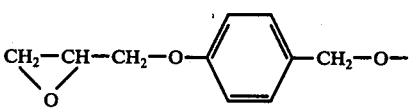

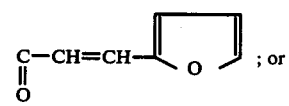

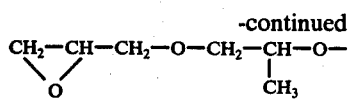

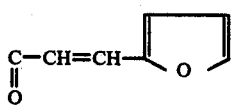

2. A furanoyl ester having the general formula (I')

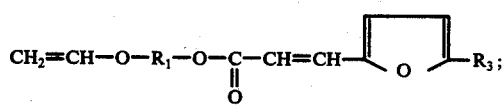

wherein $R_1$ represents

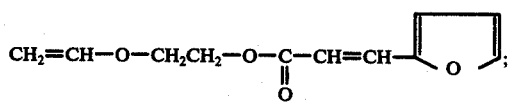

wherein $R_3$ represents a hydrogen atom, a methyl group, an ethyl group, a chlorine atom or a bromine atom; wherein $m$ is 0 or 1; and $n$ is an integer of 1 to 4.

3. The furanacroyl ester of claim 2, wherein said ester having the general formula (I') is

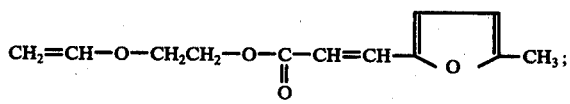

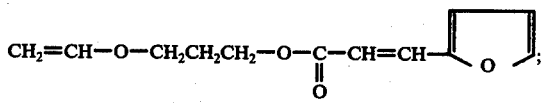

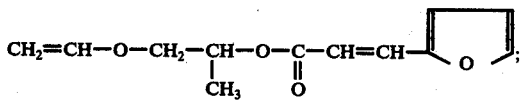

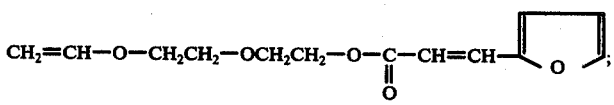

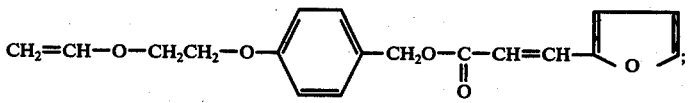

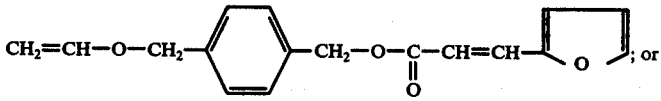

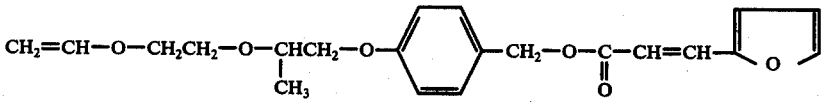

4. The furanacryloyl ester of claim 2, wherein said ester having the general formula (I') is

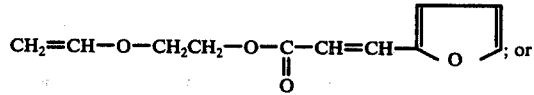

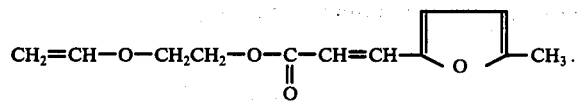
5. The furanacryloyl ester of claim 2, wherein said ester having the general formula (I') is
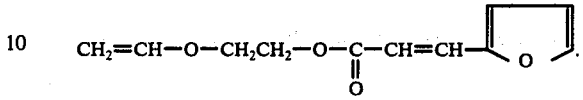
* * * * *